United States Patent [19]

Vyas et al.

[11] Patent Number: 4,874,851

[45] Date of Patent: Oct. 17, 1989

[54] 3',4'-DINITROGEN SUBSTITUTED EPIPODOPHYLLOTOXIN GLUCOSIDE DERIVATIVES

[75] Inventors: Dolatrai M. Vyas, Madison; Mark G. Saulnier, Middletown; John F. Kadow, New Haven, all of Conn.

[73] Assignee: Bristol-Meyers Company, New York, N.Y.

[21] Appl. No.: 68,376

[22] Filed: Jul. 1, 1987

[51] Int. Cl.$^4$ .............................................. C07H 15/24
[52] U.S. Cl. ................................. 536/17.2; 536/17.9; 536/18.1; 514/908
[58] Field of Search .................... 536/18.1, 17.9, 17.2; 514/25, 27, 33, 35, 908

[56] References Cited

U.S. PATENT DOCUMENTS

| | | | |
|---|---|---|---|
| 3,524,844 | 8/1970 | Keller-Juslen et al. | 536/18.1 |
| 4,547,567 | 10/1985 | Umezawa et al. | 536/18.1 |
| 4,564,675 | 1/1986 | Kurabayashi et al. | 536/18.1 |
| 4,609,644 | 9/1986 | Nemec | 514/27 |
| 4,716,221 | 12/1987 | Umezawa et al. | 536/18.1 |
| 4,757,138 | 7/1988 | Fujii et al. | 536/18.1 |

OTHER PUBLICATIONS

Holthuis, J. J. M. et al., J. Electroanal. Chem. Interfacial Electrochem., 1985, 184(2):317–29).

Ayres and Lim, Cancer Chemother Pharmacol, 1982, 7:99–101.

*Primary Examiner*—Ronald W. Griffin
*Assistant Examiner*—Nancy S. Carson
*Attorney, Agent, or Firm*—Mollie M. Yang

[57] ABSTRACT

The present invention provides novel 3',4'-dinitrogen substituted epipodophyllotoxin glucoside derivatives useful as antitumor agents.

18 Claims, No Drawings

3',4'-DINITROGEN SUBSTITUTED EPIPODOPHYLLOTOXIN GLUCOSIDE DERIVATIVES

BACKGROUND OF THE INVENTION

1. Field of the Invention

The present invention relates to novel dinitrogen substitued derivatives of epipodophyllotoxin glucosides, to their therapeutic anti-tumor use, and to pharmaceutical dosage forms containing these new agents.

2. Description of the Related Art

Etoposide (VP-16, Ia) and teniposide (VM-26, Ib) are clinically useful anticancer agents derived from the naturally occurring lignan, podophyllotoxin (II). The numbering system used for nomenclature purpose is shown in Formula II. Etoposide and teniposide are epipodophyllotoxin

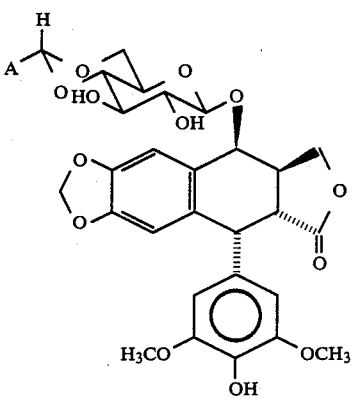

Ia: A = CH$_3$
Ib: A = 2-thienyl

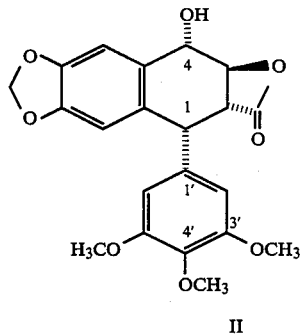

II derivatives; epipodophyllotoxin being the epimer of podophyllotoxin at the 4-position. Etoposide and teniposide are active in the treatment of a variety of cancers including small cell lung cancer, non-lymphocytic leukemia, and non-seminomatous testicular cancer (AMA Drug Evaluation, 5th Edition, American Medical Association, 1983, Chicago, Ill., p. 1554-5).

Etoposide and teniposide, and methods for producing them, are disclosed in U.S. Pat. No. 3,524,844 to Keller-Juslen et al. Etoposide 3',4'-quinone (IIIa) has been generated from electrochemical oxidation of etoposide (Holthuis J. J. M., et al, *J. Electroanal. Chem. Interfacial Electrochem.*, 1985, 184(2): 317-29). The preparation of the quinone III by chemical oxidation is disclosed in U.S. Pat. No. 4,609,644 to Josef Nemec. Epipodophyllotoxin 3',4'-quinone derivatives III wherein A and Y have the definition given hereinbelow for Formula IV, serve as the starting material for our preparation of the nitrogen containing epipodophyllotoxin derivatives of the present invention.

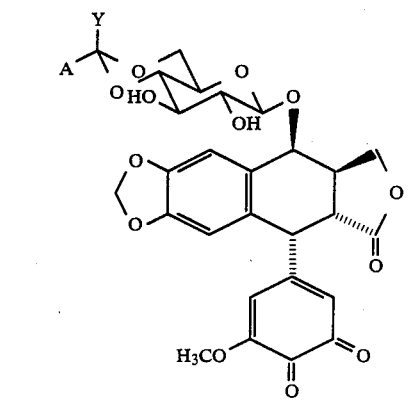

III
IIIa: A = CH$_3$; Y = H.

Ayres and Lim in *Cancer Chemother Pharmacol*, 1982, 7: 99-101 discloses the podophyllotoxin having the formula

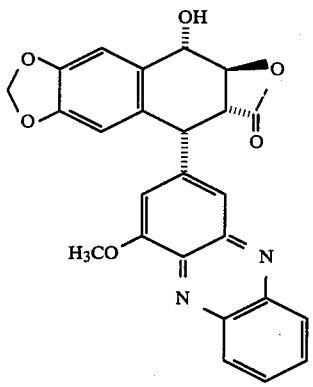

SUMMARY OF THE INVENTION

The present invention relates to antitumor compounds having the formula IV

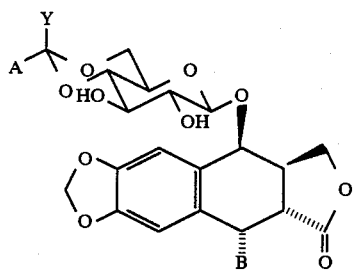

wherein wherein
Y is H and A is selected from the group consisting of (C$_{1-10}$)alkyl; (C$_{2-20}$)alkenyl; (C$_{5-6}$)cycloalkyl; 2-furyl; 2-thienyl; aryl, aralkyl, and aralkenyl, wherein each of the aromatic rings may be unsubstituted or substituted with one or more groups selected from halo, ($C_{1-8}$)alkyl, ($C_{1-8}$)alkoxy, hydroxy, nitro, and amino; or A and Y are each ($C_{1-8}$)alkyl; or A and Y and the carbon to which they are attached join to form a ($C_{5-6}$) cycloalkyl group; and B is selected from the group consisting of

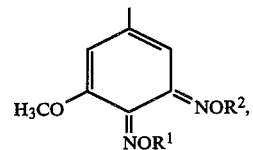

IVa

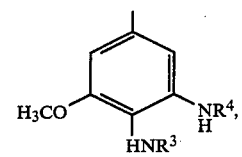

IVb

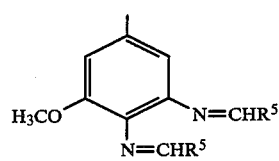

IVc

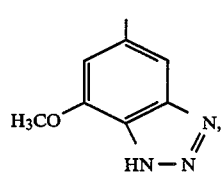

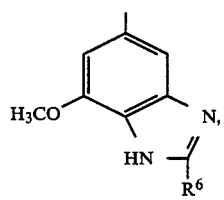

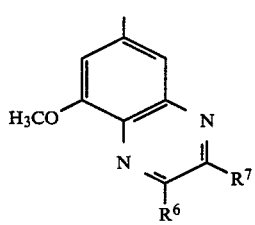

and

IVd

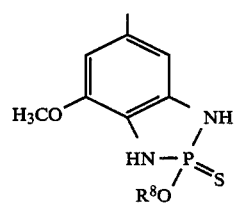

wherein $R^1$ and $R^2$ are independently selected from the group consisting of ($C_{1-5}$)alkyl, aryl, and aryl($C_{1-5}$)alkyl; $R^3$ and $R^4$ are independently H, ($C_{1-5}$)alkanoyl, or halo-substituted ($C_{2-5}$)alkanoyl; $R^5$ is aryl, aryl substituted with one or more groups selected from ($C_{1-5}$)alkoxy and nitro, or heteroaryl; $R^6$ and $R^7$ are each H or ($C_{1-5}$)alkyl; $R^8$ is ($C_{1-5}$)alkyl or ($C_{1-5}$)alkyl substituted with one or more groups selected from the group consisting of hydroxy, alkoxy, alkanoyloxy, cyano, amino, alkylamino, dialkylamino, carboxy, alkylthio, mercapto, alkanoylamino, alkanoyl, carbamoyl, and halo; and X is oxygen or sulfur.

It is to be understood that the structural formulas representing the B substituent depicted in the specification and in the claims are meant to encompass all diastereomeric and/or tautomeric forms where such are possible.

DETAILED DESCRIPTION OF THE INVENTION

The starting material for the present invention, the 3',4'-quinone III may be prepared by reacting an oxidizing agent with a 4'-demethylepipodophyllotoxin-β-D-glucoside derivative I. The method is described in U.S. Pat. No. 4,609,644 which is hereby incorporated by reference.

One aspect of the present invention provides bis-oxime ethers of Formula V wherein A, Y, $R^1$ and $R^2$ are as defined above.

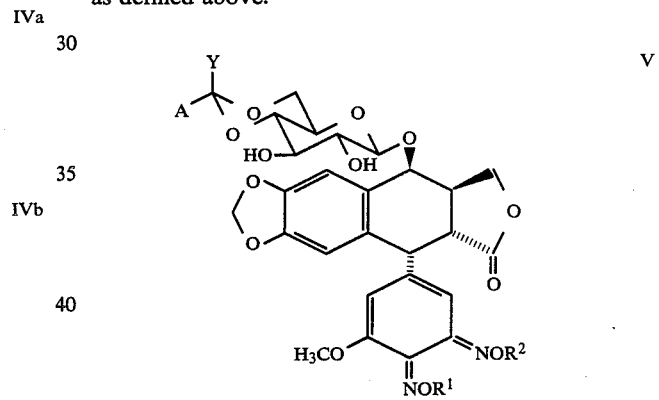

V

A preferred embodiment provides compound of Formula V wherein $R^1$ and $R^2$ are selected from the group consisting of ($C_{1-5}$)alkyl and aryl($C_{1-5}$)alkyl, with methyl and phenylmethyl being the most preferred groups.

Bis-oxime ethers of Formula V may be prepared by reacting an 3',4'-quinone III with an excess amount of an O-substituted hydroxylamine, or an acid addition salt thereof, in a suitable organic solvent such as pyridine. The reaction is preferably carried out at elevated temperature for a period sufficient to convert the starting material to the bis-oxime ether; typically such reaction time is 24 hours or more. The products thus formed may be isolated and purified by conventional techniques, e.g. flash chromatography; or alternatively, they may be reduced directly, without first being isolated, to the corresponding 3',4'-diamino compound of Formula VI.

Accordingly, a further aspect of the present invention provides the diamino compound of Formula VI wherein A and Y are as previously defined, and pharmaceutically acceptable acid addition salts thereof.

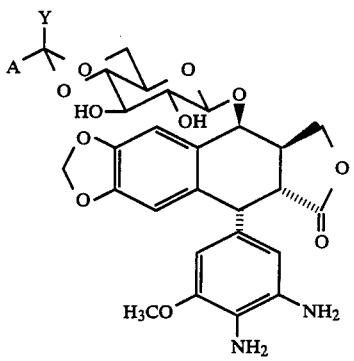

VI

The diamine of Formula VI may be prepared by reduction of the bis-oxime ether of Formula V; and as mentioned above, either a purified compound of Formula V or the crude product may be used. Reduction of the bis-oxime ether may be effected by conventional methodologies, e.g. a mild chemical reducing agent, or hydrogenation in the presence of a suitable catalyst such as Pt, Pd, Ni, Ru or Rh. Catalytic hydrogenation is preferably employed.

The diamino compounds of Formula VI may be further derivatized to provide for example, amides, imines, and heterocyclic compounds as defined for Formula IV. The reactions are generally carried out in inert organic solvents such as tetrahydrofuran, dichloromethane, or chloroform, under conditions that are appropriate for achieving the desired products. Products may be isolated and purified using known methods such as recrystallization and various chromatographic techniques.

Thus, according to another aspect of the invention amides of Formula VII are provided wherein A, Y, $R^3$, and $R^4$ are as previously defined, except $R^3$ and $R^4$ are not both H.

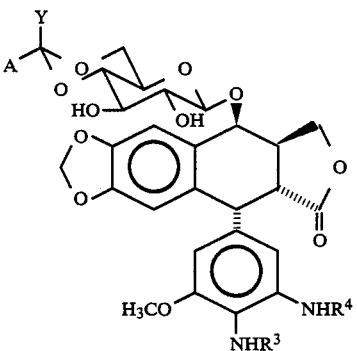

VII

A preferred embodiment provides compounds of Formula VII wherein $R^3$ and $R^4$ are both ($C_{1-5}$)alkanoyl or halo-substituted ($C_{1-5}$)alkanoyl.

Amide derivatives may be prepared by conventional acylating methodologies well known to a person of ordinary skill in synthetic organic chemistry. Suitable acylating agents include, but are not limited to, carboxylic acid, preferably in the presence of a condensing agent such as dicyclohexylcarbodiimide (DCC); an acid halide; a symmetrical or unsymmetrical anhydride; or a reactive ester or amide. In general, in preparing amide derivatives using an acid halide or an anhydride the reactions are preferably carried out at below room temperature and in the range of from about −20° C. to about 10° C. In the foregoing discussion, bis acylated derivatives are preferentially obtained when the reaction is carried out in the presence of a base and when the acylating agent is used in a molar amount at least twice that of the diamine compound of Formula VII; suitable bases are e.g. pyridine, triethylamine, diisopropyl ethylamine, and dimethylaminopyridine. When the acylating agent is used in an amount equivalent to that of the diamine compound and without the base, a mixture of 3′- and 4′-mono acylated derivatives are obtained.

According to another aspect of the present invention, there are provided bis-imino compounds of Formula VIII wherein A, Y, and $R^5$ are as previously defined.

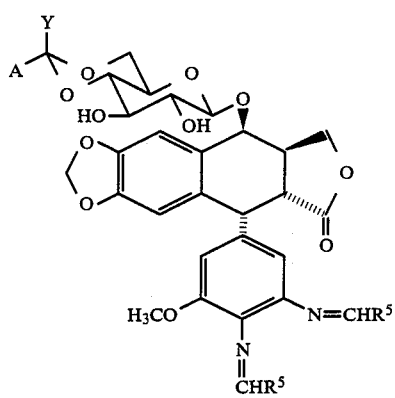

VIII

Bis-imino compounds of Formula VIII may be formed when diamino compounds of Formula VI are reacted with an excess amount of aldehyde at room temperature preferably in the presence of an acid catalyst such as p-toluenesulfonic acid, and also preferably employing a method for water removal; suitable methods therefor include the use of a dehydrating agent such as molecular sieves, or the use of azeotropic distillation. Compounds of Formula VIII are frequently labile, and a preferred method for their isolation is by chromatography using neutral alumina.

According to another aspect of the invention, there are provided compounds of Formula IV wherein B represents the heterocyclic groups IVa to IVd.

Thus, diazotization of 4′,5′-diamino compounds of Formula VI provides the corresponding triazole derivative (Formula IVa). Imidazole derivatives (Formula IVb) may be prepared by reacting the diamino compounds with trialkyl orthoesters. Reaction of the diamino compounds with a 1,2-dioxo alkane provides pyrazine derivatives (Formula IVc). Reaction of the diamino compounds with dihaloalkylphosphate or dihaloalkylthiophosphate in the presence of an organic base such as pyridine provides the corresponding cyclic phosphamide or thiophosphamide derivatives (Formula IVd), respectively.

BIOLOGICAL ACTIVITY

Representative compounds of the present invention were evaluated for their antitumor activity in in vitro cytotoxicity assay against human and murine tumor cell lines, as well as against transplantable murine P388 leukemia.

P388 Leukemia.

Female $CDF_1$ mice were implanted intraperitoneally with a tumor inoculum of $10^6$ ascites cells of P388 murine leukemia and treated with various doses of a test compound; four mice were used for each dose level and ten were used as saline-treated control. The compounds were administered by intraperitoneal injection on days 5 and 8 (day 1 being the day of tumor implantation). Antitumor activity was expressed as % T/C which is the ratio of the median survival time (MST) of drug-treated group to the MST of saline-treated control group. A compound showing a % T/C value of 125 or greater is generally considered to have significant antitumor activity in the P388 test. The experiment lasted 31 days at the end of which time the number of survivors was noted. Table I presents the results of the above-described evaluation; only the maximum % T/C and the dose showing the maximum effect are reported.

TABLE I

Antitumor activity against P388 Leukemia

| Compound of Example | Dose (mg/kg/inj) | Max. % T/C |
|---|---|---|
| 1 | 100 | 126 |
| 2 | ≧200 | 175 (270) |
| 3 | >100 | 216 |
| 4 | >160 | 105 (270) |
| 10 | ≧180 | 145 (270) |
| 17 | >180 | 125 (≧370) |
| 18 | >140 | 115 (270) |
| 20 | >180 | 110 (270) |
| 21 | ≧120 | 145 (270) |

*The values in parentheses are the values obtained with etoposide as the positive control in the same experiment.

Cytotoxicity Assay

The in vitro cytotoxicity assay involved growing various mammalian tumor cells, including human tumor cells, on microtitre plates employing established tissue culture methods. The concentration of each compound required to inhibit cell growth by 50% ($IC_{50}$) was then determined by a four-fold serial dilution technique. The validity of the method has been supported by a report published in the "Proceedings of the American Association for Cancer Research", 1984, 25: 1891 (Abst. No. 328). Tumor cells of the following types were employed for each compound tested: B16-F10 murine melanoma; KB human nasopharyngyl; Moser human colon; SW900 human lung; M109 murine lung; and three human colon tumor cell lines namely HCT-116, HCT-VM, and HCT-VP, the latter two being resistant to teniposide (VM) and etoposide (VP), respectively. $IC_{50}$ values less than 500 μg/ml are a positive indicator of antitumor activity. Table II presents $IC_{50}$ values of various compounds of the present invention against the aforementioned cell lines.

TABLE II

In vitro cytotoxicity assay $IC_{50}$ values (μg/ml)*

| B-16-F10 | HCT-116 | HCT/VM46 | HCT/VP35 | MOSER | SW900 |
|---|---|---|---|---|---|
| Example 17 | | | | | |
| 45 | 53 | 64 | 84 | 91 | 78 |
| 55 | 62 | 88 | 82 | 88 | 89 |

| B-16-F10 | HCT-116 | MOSER | SW900 |
|---|---|---|---|
| Example 2 | | | |
| 29 | 84 | 54 | >250 |
| 51 | 91 | 40 | >250 |
| Example 4 | | | |
| 116 | >250 | 106 | >250 |
| 98 | >250 | 123 | >250 |
| Example 10 | | | |
| 59 | 81 | 31 | >250 |

TABLE II-continued

In vitro cytotoxicity assay $IC_{50}$ values (μg/ml)*

| 100 | 103 | 65 | >250 |
|---|---|---|---|
| Example 18 | | | |
| 82 | >250 | 116 | >250 |
| 55 | >250 | 115 | >250 |
| Example 20 | | | |
| 118 | 103 | 113 | >250 |
| 113 | 99 | 90 | >250 |
| Example 21 | | | |
| 23 | 20 | 21 | >250 |
| 17.9 | 26 | 23 | >250 |

| B-16-F10 | HCT-116 | KB | MOSER | M109 |
|---|---|---|---|---|
| Example 1 | | | | |
| 14.5 | 7.4 | 37 | 43 | 83 |
| 14.1 | 17.4 | 28 | 11 | 59 |
| Example 3 | | | | |
| 59 | 108 | 290 | 87 | 104 |
| 146 | 102 | 91 | 91 | 87 |

From the data presented above it is observed that although some of the analogs tested do not show activity against in vivo P388 leukemia, they may all be considered active against various solid tumors in in vitro cytotoxicity assays.

Accordingly, this invention provides a method for inhibiting tumor cell growth which comprises administering an effective tumor-inhibiting dose of an antitumor compound of formula IV to a tumor bearing host.

Another aspect of this invention provides a pharmaceutical composition which comprises an effective tumor-inhibiting amount of an antitumor compound of formula IV and a pharmaceutically acceptable carrier. These compositions may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preprations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are for illustrative purposes only should not be construed as limiting the scope of the invention.

In the following examples, all temperatures are given in degrees Centigrade. Melting points were recorded on a Thomas-Hoover capillary melting point apparatus and are uncorrected. $^1$H NMR spectra were recorded either on a Bruker WM 360 or a Varian VX2 200 spectrophotometer (using $CDCl_3$ as an internal reference). Chemical shifts are reported in δ units and coupling constants in Hertz. Splitting patterns are designated as follows: s, singlet; d, doublet; t, triplet, q, quartet; m, multiplet; bp, broad peak; and dd, doublet of doublet. Infrared spectra were determined either on a Beckman Model 4240 or a Perkin-Elmer 1800 Fourier Transform Infrared Spectrophotometer and are reported in reciprocal centimeters (cm$^{-1}$). Thin-layer chromatography (TLC) was carried out on precoated silica gel plates (60F-254) using UV light and/or iodine vapors as visualizing agents. High and low resolution mass spectra were recorded on KRATOS MS 50 and KRATOS MS 25RFA Spectrophotometer, respectively. "Flash Chromatography" refers to the method described by Still (Still, W. C. et al, J. Org. Chem., 1978, 43: 2923) and was carried out using either E. Merck silica gel (200–400 mesh) or Woelm silica gel (32–63 μm). All evaporations of solvents were performed under reduced pressure. The term "ETOP" is used to represent the structural fragment

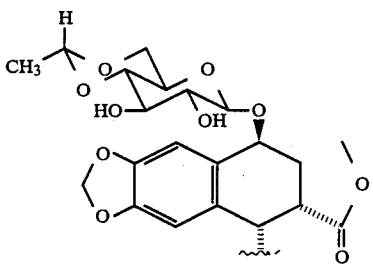

EXAMPLE 1

4'-Dehydroxy-3'-demethoxy-etoposide 3',4'-bis-O-benzyloxime

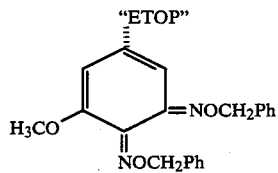

Solid O-benzyl-hydroxylamine hydrochloride (2.80 g, 17.5 mmol) was added to a solution of etoposide 3',4'-quinone (2.50 g, 4.37 mmol) in pyridine (75 ml). The mixture was stirred at 54° C. for 43 hrs and then at 60°-70° C. for an additional 15 min. Pyridine was removed under reduced pressure and the residue was dissolved in CH$_2$Cl$_2$ (250 ml) and extracted with a mixture of H$_2$O (200 ml) and 1N HCl (70 ml). The aqueous layer was further extracted with CH$_2$Cl$_2$ (2×15 ml) and the combined extracts were washed with H$_2$O (100 ml) and brine (150 ml) and dried over Na$_2$SO$_4$. After evaporation of the solvent, 3.7 g of a yellow orange solid was obtained which was purified by flash chromatography on silica gel. Elution with 1% CH$_3$OH in CH$_2$Cl$_2$ produced 2.10 g (61.4%) of the pure title compound as a yellow orange solid, mp 152°-156° C.

$^1$H NMR (CDCl$_3$) δ7.38–7.11 (m, 10H), 6.67 (s, 1H), 6.53 (s, 1H), 6.02 (d, 1H), 5.96 (d, 2H), 5.90 (d, 1H), 5.46 (s, 2H), 5.13 (s, 2H), 4.82 (d, 1H, J=3.5 Hz), 4.73 (q, 1H, J=5 Hz), 4.61 (d, 1H, J=7.6 Hz), 4.42 (dd, 1H), 4.30–4.24 (m, 2H), 4.14 (dd, 1H, J=3.9 and 10.4 Hz), 3.79 (s, 3H), 3.74–3.69 (m, 1H), 3.57–3.51 (m, 1H), 3.43–3.37 (m, 1H), 3.32–3.29 (m, 2H), 3.23 (dd, 1H, J=5.5 and 14.1 Hz), 2.89–2.82 (m, 1H), 2.64 (d, 1H, J=2 Hz, OH), 2.30 (d, 1H, J=2.3 Hz, OH), 1.37 (d, 3H, J=5 Hz).

EXAMPLE 2

4'-Dehydroxy-3'-demethoxy-etoposide 3',4'-bis-O-methyloxime

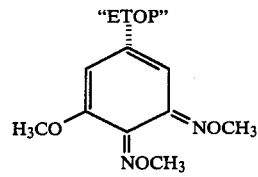

Solid methoxylamine hydrochloride (3.0 g, 35 mmol) was added to a solution of etoposide o-quinone (5.0 g, 8.73 mmol) in pyridine (50 ml) stirring at room temperature under N$_2$. The dark red solution immediately changed to a dark orange solution upon addition. The reaction mixture was heated for 24 hours at 60° C. and then for an additional 24 hours at 75° C. The pyridine was removed by evaporation in vacuo. Flash chromatography on silica gel using 4% MeOH in CH$_2$Cl$_2$ as eluent provided 4.73 g of yellow-orange solid (86%), mp 205°-210°.

IR (KBr) 3480 (b), 2920, 1780, 1495 cm$^{-1}$.

$^1$H NMR (CDCl$_3$) δ6.79 (s, 1H), 6.53 (s, 1H), 6.00 (m, 3H), 5.83 (s, 1H), 4.88 (d, J=3.2 Hz, 1H), 4.75 (m, 1H), 4.64 (d, J=7.0 Hz, 1H), 4.50–4.05 (m, 4H), 4.20 (s, 3H), 3.95 (s, 3H), 3.79 (s, 3H), 3.75–3.20 (m, 6H), 2.94 (m, 1H), 1.38 (d, J=5.0 Hz, 3H).

MS (FAB) m/e=631 (M+H)$^+$.

EXAMPLE 3

4'-Dehydroxy-3'-demethoxy-3',4'-diamino etoposide

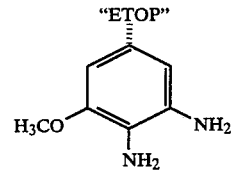

A solution of 4'-dehydroxy-3'-demethoxy-etoposide 3',4'-bis-O-benzyloxime (2.00 g, 2.55 mmol) in reagent alcohol (100 ml) and ethyl acetate (65 ml) was treated with 20% palladium hydroxide on carbon and hydrogenated at 65 psi for 1.5 hrs. The mixture was filtered through a pad of Celite and washed with ethyl acetate. The filtrate was concentrated and purified by flash chromatography on silica gel. Elution with 2% CH$_3$OH in CH$_2$Cl$_2$ followed by 5% CH$_3$OH in CH$_2$Cl$_2$ gave 1.12 g (76.7%) of the pure title compound as an off-white solid, mp 235°-240° C. (dec, darkens at 200° C.). Trituration with ether gave the analytical sample.

IR (KBr) 3420, 1775, 1505, 1485, 1230, 1165, 1095, 1075, 1040, 1005, 930 cm$^{-1}$.

$^1$H NMR (CDCl$_3$) δ6.78 (s, 1H), 6.54 (s, 1H), 6.35 (d, 1H, J=1.3 Hz), 5.95 (d, 2H), 5.70 (d, 1H, J=1.3 Hz), 4.86 (d, 1H, J=3.3 Hz), 4.73 (q, 1H, J=5 Hz), 4.63 (d, 1H, J=7.6 Hz), 4.52 (d, 1H, J=5.1 Hz), 4.38 (dd, 1H), 4.20–4.13 (m, 2H), 3.79–3.73 (m, 1H), 3.75 (s, 3H), 3.59–3.53 (m, 1H), 3.41 (dd, 1H), 3.35–3.31 (m, 2H), 3.20 (dd, 1H, J=5.1 and 14.1 Hz), 2.98–2.88 (m, 1H), 1.38 (d, 3H, J=5 Hz).

Anal. Calcd for $C_{28}H_{32}N_2O_{11}$: C, 58.73; H, 5.63; N, 4.89. Found: C, 57.37; H, 5.77; N, 4.78.

EXAMPLE 4

4′-Dehydroxy-3′-demethoxy-3′,4′-bis-acetylamino etoposide

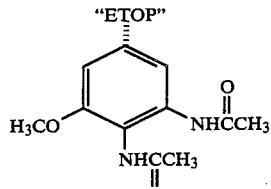

Acetic anhydride (68 μl, 0.71 mmol) was added dropwise to a magnetically stirred solution of diamino etoposide (product of Example 3, 0.200 g, 0.35 mmol) and pyridine (60 μl, 0.74 mmol) in $CH_2Cl_2$ (5 ml) at 2° C. under an atmosphere of $N_2$. Stirring was continued for 4 hours whereupon TLC analysis (5% MeOH in $CH_2Cl_2$) showed the presence of a new less polar product and the absence of starting material. The reaction mixture was poured into water, extracted with three portions of $CH_2Cl_2$, dried over $MgSO_4$, and purified by flash chromatography using 4% MeOH in $CH_2Cl_2$ as eluent on silica gel to provide 0.111 g (76%) of off white solid, mp. (slow decomposition to a foam above 217° C.).

IR (KBr) 3440 (b), 2930, 1780, 1679, 1490 cm$^{-1}$.

$^1$H NMR (CDCl$_3$) δ8.84 (s, 1H), 7.01 (s, 1H), 6.80 (s, 1H), 6.48 (s, 1H), 6.47 (s, 1H), 5.95 (d, J=5.8 Hz, 2H), 4.94 (d, J=3.3 Hz, 1H), 4.72 (m, 1H), 4.64 (d, J=7.7 Hz, 1H), 4.39 (t, J=9.3 Hz, 1H), 4.24 (t, J=9.2 Hz, 1H), 4.15 (m, 1H), 3.88 (s, 3H), 3.73 (t, J=8.7 Hz, 1H), 3.53 (t, J=9.6 Hz, 1H), 3.40 (t, J=8.2 Hz, 1H), 3.40–3.10 (m, 3H), 2.71 (bs, 1H, [sugar-OH]), 2.42 (bs, 1H, [sugar-OH]), 2.24 (s, 3H), 2.02 (s, 3H), 1.37 (d, J=5.1 Hz, 3H).

MS (FAB) m/e=657 (M+H)+.

If the general procedure described in Example 4 is followed using the acylating agent listed below in place of acetic anhydride, the corresponding bis-acylated compounds are obtained.

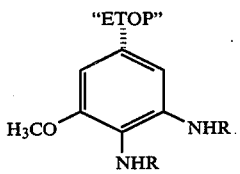

| Example | Acylating Agent | Product |
|---|---|---|
| 5 | acetic formic anhydride | R = formyl |
| 6 | trifluoroacetic anhydride | R = trifluoroacetyl |

If the general procedure described in Example 4 is repeated using the acylating agent listed below in a molar amount equivalent to that of 3′,4′-diaminoetoposide and in the absense of pyridine, a mixture of the corresponding 4′- and 3′-monoacylated derivatives is obtained.

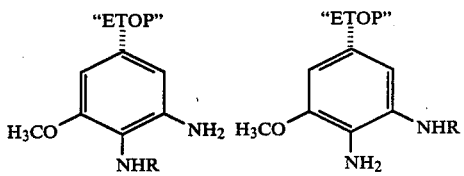

| Example | Acylating Agent | Product |
|---|---|---|
| 7 | acetic anhydride | R = acetyl |
| 8 | acetic formic anhydride | R = formyl |
| 9 | trifluoroacetic anhydride | R = trifluoroacetyl |

EXAMPLE 10

4′-Dehydroxy-3′-demethoxy-3′,4′-bis-(4-pyridylmethylene) amino Etoposide

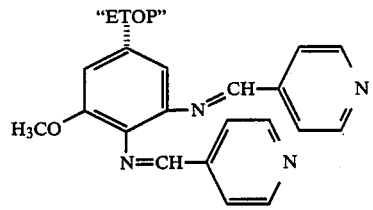

A solution of 3′,4′-diamino etoposide (product of Example 3, 181 mg, 0.316 mmol) in dry $CH_2Cl_2$ (35 ml) under $N_2$ was treated with activated 4A molecular sieves (2.25 g) and 4-pyridine carboxaldehyde (4.56 g 42.6 mmol). The mixture was stirred at room temperature for 26 days and then applied directly to the top of a 2 cm column filled with 6½ inches of neutral alumina. Sequential elution with 200 ml each of 50% and 75% EtOAc in $CH_2Cl_2$ and then EtOAc and 10–15% $CH_3OH$ in EtOAc removed the excess aldehyde and other impurities. Finally, the title compound was eluted with 130 ml of $CH_3OH$. After evaporation in vacuo, the solids were dissolved in EtOAc (75 ml) and $CH_3OH$ (2 ml), filtered, and evaporated. The resulting yellow solid was dissolved in 2–3% $CH_3OH$ in $CH_2Cl_2$ and filtered through a 0.45 micron filter to give a clear yellow solution. Rotary evaporation and drying at 0.1 torr provided 145 mg (61%) of the pure title compound as a yellow-orange solid. The 360 MHz $^1$H NMR spectrum indicated a ca 65:35 mixture of isomers tentatively assigned as the 3′-Z, 4′-E and the 3′-E, 4′-E based purely on steric considerations.

Partial $^1$H NMR (CDCl$_3$) δ8.73–8.66 (m, 4H), 8.40 (s, 1H), 8.28 (s, 1H), 7.65–7.57 (m, 4H), 6.96 (s, 1H), 6.82 (s, 1H), 6.57 (s, 1H), 6.28 (d, 1H), 6.01–5.94 (m, 2H), 4.17 (s, 3H), 1.24 (d, 3H), 1.23 (d, 3H).

If the general procedure of Example 10 is repeated with the aldehydes listed below in place of 4-pyridinecarboxaldehyde, the corresponding bis-imino compounds are obtained.

"ETOP"

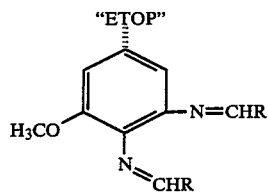

| Example | Aldehyde | Product (R=) |
| --- | --- | --- |
| 11 | benzaldehyde | phenyl |
| 12 | 4-methoxybenzaldehyde | 4-methoxyphenyl |
| 13 | 3,4,5-trimethoxybenz-aldehyde | 3,4,5-tri-methoxyphenyl |
| 14 | 3-thiophenecarboxaldehyde | 3-thienyl |
| 15 | 2-furancarboxaldehyde | 2-furyl |
| 16 | 3-nitrobenzaldehyde | 3-nitrophenyl |

EXAMPLE 17

4'-Dehydroxy-3'-demethoxy-etoposide 3',4'-triazole

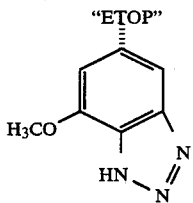

Sodium nitrite (26.8 mg, 0.388 mmol) was added to a solution of the 3',4'-diamino etoposide (product of Example 3, 169.1 mg, 0.2953 mmol) in dry THF (4 ml) and glacial acetic acid (0.75 ml). The mixture was stirred at room temperature for 3 hrs, poured into cold saturated aqueous sodium bicarbonate (100 ml), and extracted with $CH_2Cl_2$ (2×50 ml). The combined extracts were washed with brine (50 ml) and dried over $Na_2SO_4$. Rotary evaporation followed by crystallization from $CH_2Cl_2$ (3-5 ml) produced 128.1 mg (74.3%) of the pure title compound as a colorless solid, mp 245°-250° C.

IR (KBr) 3445, 1775, 1625, 1605, 1507, 1488, 1455, 1400, 1345, 1240, 1165, 1100, 1085, 1045, 1010, 945, 880, 772, 705 cm$^{-1}$.

UV ($CH_3OH$) $\lambda$max 287 nm (log $\epsilon$=3.909).

$^1$H NMR ($CDCl_3$) $\delta$7.25 (d, 1H), 6.84 (s, 1H), 6.66 (d, 1H), 6.51 (s, 1H), 5.98 (s, 2H), 4.91 (d, 1H, J=3.3 Hz), 4.78 (d, 1H, J=5.3 Hz), 4.73 (q, 1H, J=4.9 Hz), 4.65 (d, 1H, J=7.5 Hz), 4.42 (dd, 1H), 4.20–4.14 (m, 2H), 4.04 (s, 3H), 3.73 (m, 1H), 3.56 (m, 1H), 3.44 (m, 1H), 3.40–3.32 (m, 3H), 2.94 (m, 1H), 1.38 (d, 3H, J=4.9 Hz).

MS (FAB) m/e=584 (M+H)$^+$, 378 (M-sugar)$^+$.

Anal. Calcd for $C_{28}H_{29}N_3O_{11}$: C, 57.63; H, 5.01; N, 7.20. Found: C, 57.81; H, 4.90; N, 7.11.

EXAMPLE 18

4'-Dehydroxy-3'-demethoxy etoposide 3',4'-imidazole

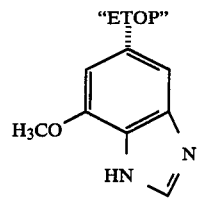

A solution of 3',4'-diamino etoposide (product of Example 3, 182 mg, 0.318 mmol) in $CH_2Cl_2$ (10 ml) was treated with trimethyl orthoformate (500 mg, 4.7 mmol) and p-toluenesulfonic acid monohydrate (1.3 mg) and the mixture was stirred at room temperature for 6 days. The resulting title compound was collected by filtration as an off-white solid (28.7 mg, 15.5%). The remaining filtrate was treated with trimethyl orthoformate (2 ml) and p-toluenesulfonic acid monohydrate (8 mg) and stirred at room temperature for 12 days. Following workup with ethyl acetate and aqueous sodium bicarbonate, flash chromatography of the resulting crude material using 5% and then 10% $CH_3OH$ in $CH_2Cl_2$ provided 53.6 mg (28.9%) of additional pure title compound.

IR (KBr) 3435, 1775, 1633, 1603, 1490, 1390, 1340, 1240, 1165, 1100, 1080, 1040, 1010, 940, 703 cm$^{-1}$.

$^1$H NMR (d$_6$-DMSO) $\delta$8.08 (broad s, 1H), 7.02 (s, 1H), 6.61 (m, 1H), 6.54 (s, 1H), 6.48 (d, 1H), 6.02 (s, 2H), 5.24 (m, 2H), 4.95 (d, 1H), 4.72–4.68 (m, 2H), 4.56 (d, 1H), 4.29–4.22 (m, 2H), 4.08 (dd, 1H), 3.86 (s, 3H), 3.50 (dd, 1H), 3.38–3.03 (m, 4H), 2.95–2.85 (m, 1H), 1.23 (d, 3H, J=5 Hz).

UV ($CH_3OH$) $\lambda$max 243 (sh) and 282 (log $\epsilon$=3.765) nm.

MS (FAB) m/e=583 (M+H)$^+$, 378 (m-sugar)$^+$.

EXAMPLE 19

4'-Dehydroxy-3'-demethoxy etoposide 3',4'-(2-methylimidazole)

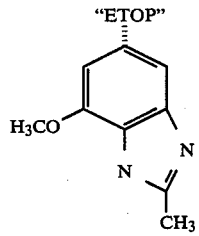

If the procedure of Example 18 is repeated using trimethyl orthoacetate in place of the orthoformate, the title compound is obtained.

EXAMPLE 20

4'-Dehydroxy-3'-demethoxy-etoposide 3',4'-(2,3-dimethylpyrazine)

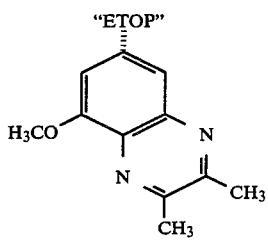

A solution of 3',4'-diamino etoposide (product of Example 3, 225 mg, 0.393 mmol) in dry CH$_2$Cl$_2$ (15 ml) was treated dropwise over 1 min with neat 2,3-butanedione (56 mg, 0.65 mmol). After 5–10 min at room temperature the reaction mixture was cooled to 0° C. and the product was collected by filtration, washed with cold CH$_2$Cl$_2$ and dried to give 163 mg. (66.7%) of the analytically pure title compound as a white solid.

IR (KBr) 3450, 1776, 1620, 1575, 1508, 1490, 1387, 1342, 1236, 1203, 1165, 1117, 1095, 1080, 1040, 1007, 936, 892, 878, 700 cm$^{-1}$.

$^1$H NMR (d$_6$-DMSO) δ7.14 (d, 1H, J=1.2 Hz), 7.05 (s, 1H), 6.68 (d, 1H, J=1.2 Hz), 6.58 (s, 1H), 6.04 (s, 2H), 4.97 (s, 1H, J=3.4 Hz), 4.80 (d, 1H, J=5.6 Hz), 4.71 (q, 1H, J=5 Hz), 4.55 (d, 1H, J=7.8 Hz), 4.31–4.21 (m, 2H), 4.08 (dd, 1H), 3.91 (s, 3H), 3.53–3.46 (m, 2H), 3.40–3.05 (m, 4H), 2.92–2.83 (m, 1H), 2.61 (s, 3H), 2.56 (s, 3H), 1.23 (d, 3H, J=5 Hz).

UV (CH$_3$OH) λmax (log ε) 259 (4.661), 292 (3.778), 326 (3.681).

Anal. Calcd for C$_{32}$H$_{34}$N$_2$O$_{11}$: C, 61.73; H, 5.50; N, 4.50. Found: C, 61.33; H, 5.24; N, 4.45.

EXAMPLE 21

4'-Dehydroxy-3'-demethoxy etoposide 3',4'-ethylthiophosphamide

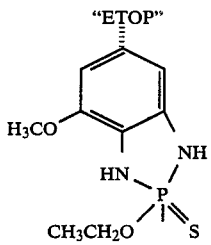

Ethyl dichlorothiophosphate (49 μl, 0.37 mmol) was added to a solution of 3',4'-diamino etoposide (product of Example 3, 0.20 g, 0.35 mmol) and pyridine (0.12 ml, 1.4 mmol) in CH$_2$Cl$_2$ (4 ml) at room temperature. The reaction was refluxed for 2.5 hours and then stored at $-10°$ C. overnight. Flash chromatography on silica gel using 3% MeOH in CH$_2$Cl$_2$ provided 0.030 g (13%) of off-white solid (TLC R$_f$ just above that of the starting diamine etoposide) as a mixture of diastereomers.

IR (KBr) 3420, 2922, 1780, 1640, 1601, 1490 cm$^{-1}$.

$^1$H NMR (CDCl$_3$) δ8.61 (m, 1H), 7.7 (m, 1H), 7.31 (m, 1H), 6.79, 6.78 (s, 1H), 6.50, 6.49 (s, 1H), 5.97 (m, 2H), 5.86, 5.83 (s, 1H), 5.59–5.42 (m, 2H), 4.88 (m, 1H), 4.73 (m, 1H), 4.54 (m, 2H), 4.40 (m, 1H), 4.17 (m, 2H), 3.97 (m, 2H), 3.73, 3.72 (m, 2H), 3.44 (m, 1H), 3.31 (m, 1H), 3.27 (m, 3H), 2.87 (m, 1H), 1.36 (d, J=2.4 Hz, 3H), 1.22 (m, 3H).

MS (FAB) m/e 678 M$^+$.

EXAMPLE 22

4'-Dehydroxy-3'-demethoxy etoposide 3',4'-ethylphosphamide

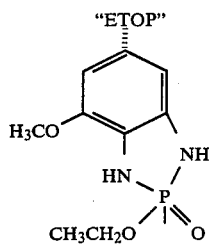

The procedure of Example 21 is repeated using ethyl dichlorophosphate in place of ethyl dichlorothiophosphate to provide the title compound.

What is claimed is:

1. A compound having the formula

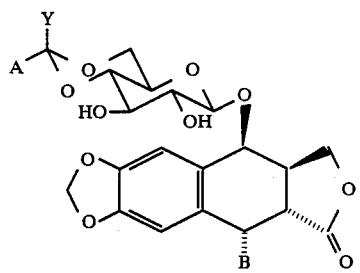

wherein Y is H and A is selected from the group consisting of (C$_{1-10}$)alkyl; (C$_{2-10}$)alkenyl; (C$_{5-6}$)cycloalkyl; 2-furyl; 2-thienyl; phenyl; and phenyl sustituted with one or more groups selected from halo, (C$_{1-8}$)alkyl, (C$_{1-8}$)alkoxy, hydroxy, nitro, and amino; or A and Y are each (C$_{1-8}$)alkyl; or A and Y and the carbon to which they are attached join to form a (C$_{5-6}$)cycloalkyl group and B is selected from the group consisting of

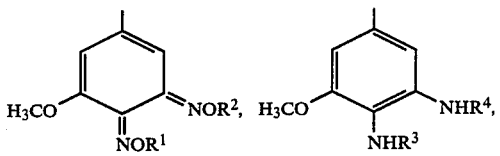

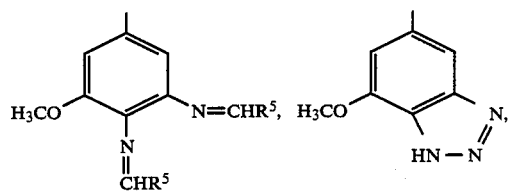

-continued

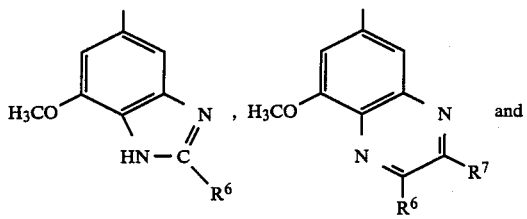

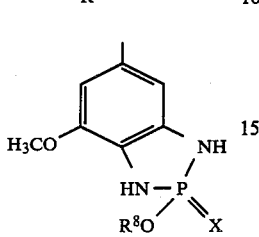

wherein $R^1$ and $R^2$ are independently selected from the group consisting of $(C_{1-5})$alkyl, phenyl, and phenyl$(C_{1-5})$alkyl; $R^3$ and $R^4$ are independently H, $(C_{1-5})$alkanoyl, or halo-substituted $(C_{2-5})$alkanoyl; $R^5$ is phenyl, phenyl substituted with one or more groups selected from $(C_{1-5})$alkoxy and nitro, or a heteroaryl selected from the group consisting of thienyl, furyl, and pyridyl; $R^6$ and $R^7$ are each H or $(C_{1-5})$alkyl; $R^8$ is $(C_{1-5})$alkyl; and X is oxygen or sulfur.

2. The compound of claim 1 wherein Y is H and A is methyl or 2-thienyl.

3. The compound of claim 2 wherein A is methyl.

4. The compound of claim 1 wherein A is methyl, Y is H and B is

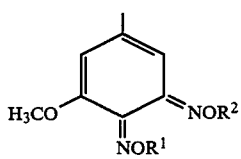

wherein $R^1$ and $R^2$ are as previously defined in claim 1.

5. The compound of claim 4 wherein $R^1$ and $R^2$ are both methyl.

6. The compound of claim 4 where $R^1$ and $R^2$ are both phenylmethyl.

7. The compound of claim 3 wherein B is

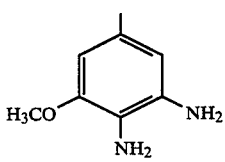

or a pharmaceutically acceptable acid addition salt thereof.

8. The compound of claim 3 wherein B is

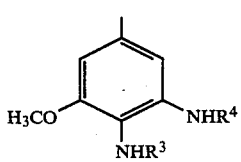

wherein $R^3$ and $R^4$ are the same and are selected from the group consisting of $(C_{1-5})$alkanoyl and halo-substituted $(C_{2-5})$alkanoyl.

9. The compound of claim 8 wherein $R^3$ and $R^4$ are each acetyl.

10. The compound of claim 1 wherein A is methyl, Y is H and B is

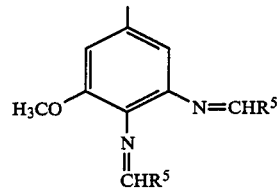

wherein $R^5$ is as previously defined in claim 1.

11. The compound of claim 10 wherein $R^5$ is 4-pyridyl.

12. The compound of claim 3 wherein B is

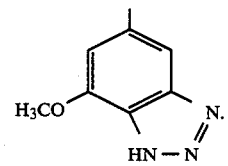

13. The compound of claim 3 wherein B is

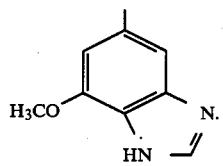

14. The compound of claim 3 wherein B is

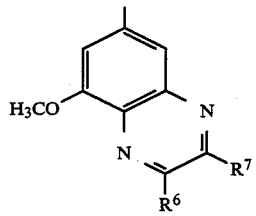

where $R^6$ and $R^7$ are independently $(C_{1-5})$alkyl.

15. The compound of claim 14 wherein $R^6$ and $R^7$ are both methyl.

16. The compound of claim 3 wherein A is methyl, Y is H and B is

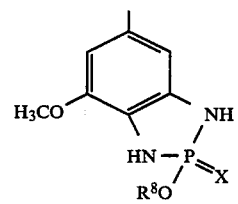

wherein X and $R^8$ are as previously defined in claim 1.

17. The compound of claim 16 wherein $R^8$ is $(C_{1-5})$alkyl.

18. The compound of claim 16 wherein X is sulfur and $R^8$ is ethyl.

* * * * *